United States Patent [19]

Kim

[11] 3,985,675

[45] Oct. 12, 1976

[54] PROCESS FOR GELLING AQUEOUS POLYOL SUSPENSIONS AND RESULTING GEL

[75] Inventor: Keun Young Kim, Chesterfield, Mo.

[73] Assignee: Monsanto Company, St. Louis, Mo.

[22] Filed: Feb. 13, 1975

[21] Appl. No.: 549,649

Related U.S. Application Data

[62] Division of Ser. No. 110,605, Jan. 28, 1971, Pat. No. 3,875,289.

[52] U.S. Cl. ................................. 252/317; 252/309; 424/65; 424/DIG. 5
[51] Int. Cl.² .......................................... B01J 13/00
[58] Field of Search ........................... 252/317, 309

[56] References Cited
UNITED STATES PATENTS

| | | | |
|---|---|---|---|
| 1,790,272 | 1/1931 | Leasman | 252/317 X |
| 2,277,854 | 3/1942 | Lecoq | 252/317 X |
| 2,563,606 | 8/1951 | Kimberlin, Jr. et al. | 252/317 X |
| 2,605,229 | 7/1952 | Marcus | 252/317 |
| 2,940,938 | 6/1960 | Blinka | 252/309 |

*Primary Examiner*—Richard D. Lovering
*Attorney, Agent, or Firm*—Herbert B. Roberts

[57] ABSTRACT

This invention relates to novel partially dehydrated amorphous calcium sodium pyrophosphate and to the production of such compounds. Also this invention relates to the process for the use of these compounds to gel aqueous solutions of some polyols and to the gels obtained therefrom.

6 Claims, No Drawings

PROCESS FOR GELLING AQUEOUS POLYOL SUSPENSIONS AND RESULTING GEL

This is a division of application Ser. No. 110,605, filed Jan. 28, 1971, now U.S. Pat. No. 3,875,289.

BACKGROUND OF THE INVENTION

1. Field of the Invention

This invention relates to novel partially dehydrated amorphous calcium sodium pyrophosphates and to processes for preparing such compounds and to the use of these compounds to gel aqueous solutions of polyols and the resulting gels.

2. Description of the Prior Art

Gels which are two-phase colloidal systems consisting of a solid and a liquid have many uses, for example, in the food areas such as dessert puddings, the pharmaceutical areas such as a medicated cream, or in rub-on sticks. Most hydrocolloids used are expensive. Some of the raw material used in preparing these gels are not available in large supplies. Some polyols, sorbitol for example, are available in large quantities at low costs. Consequently, a process for producing polyol gels would be an advancement in the art.

BRIEF DESCRIPTION OF THE INVENTION

This invention relates to polyol gels and to a process for preparing polyol gels by utilizing a novel compound, i.e., a partially dehydrated amorphous calcium sodium pyrophosphate, as a gelling agent. Another aspect of this invention is a process for preparing the novel compounds. The processes of this invention provide polyol gels which may be utilized for cosmetic and pharmaceutical purposes. The invention will be better understood from the following detailed description of the invention.

DETAILED DESCRIPTION OF THE INVENTION

The novel compounds of this invention are partially dehydrated amorphous calcium sodium pyrophosphates represented by the formula $CaNa_2P_2O_7 \cdot xH_2O$ wherein x has a value of from about 0.1 to about 2.0. This compound is used to gel aqueous solutions of some polyols as will hereinafter be set forth.

These compounds may be prepared by dehydrating calcium sodium pyrophosphate tetrahydrate. The tetrahydrate is heated at a temperature of 60° C to about 400° C, preferably from about 200° C to about 300° C. The tetrahydrate is heated until the desired amount of water of hydration is removed. The calcium sodium pyrophosphate tetrahydrate can be prepared by neutralizing a lime slurry with sodium acid pyrophosphate or by reacting a calcium salt with pyrophosphate in aqueous alkaline medium.

In most instances, at least 0.05 weight percent of partially dehydrated amorphous calcium sodium pyrophosphate must be used to gel the aqueous solutions of polyols. An amount lower than that of 0.05 weight percent usually results in unsatisfactory gelling.

There is no upper limit on the amount that may be used. For example, hard gels are obtained with 40 weight percent and even with 90 weight percent. A satisfactory operating range is from 0.1 to about 10 weight percent with 0.5 to about 5 weight percent being preferred.

As mentioned before, aqueous solution of polyols may be gelled with the novel compounds of this invention. These polyols include sorbitol, mannitol, and glycerine. Sorbitol is preferred. Such aqueous solutions of polyols contained about at least 10 weight percent of the polyols based on the total weight of the aqueous solution of polyols. Generally in amounts below 10 weight percent the aqueous solution of polyols is gelled to very weak structure. There is no upper limit on the amount of polyols that may be present, for example, gelling is obtained with up to the saturation point of aqueous solution of polyols. It is preferred to use aqueous solutions of polyols containing about 30 weight percent to about 70 weight percent based on the total weight of the aqueous solution of polyols as good gels are formed.

The aqueous solution of polyol may be gelled in any convenient vessel. The calcium sodium pyrophosphate is added to the aqueous solution of polyols. It is preferred to add the calcium sodium pyrophosphate to the aqueous solution of a polyol with intense agitation. The mixture is transferred to the desired container to gel. Various molds can be used to produce varying shapes.

The temperature at which the reaction is conducted in accordance with this invention can be conventional. For example, it can range from the freezing point of the reaction mixture to about 100° C, but the preferred operating temperature is from about −10° C to about 80° C with temperature of about room temperature to about 60° C being especially preferred.

The time required for a satisfactory degree of gelling in the process according to this invention depends upon a number of factors including temperature, concentration of polyols, degree of agitation during dispersion, presence of other ingredients, and amount of gellant utilized. In most instances, the aqueous solutions will take from about 10 minutes to 5 hours to gel the aqueous solutions of polyols.

However, when a soluble ortho or pyrophosphate is added in an amount of from about 800 ppm to 1500 ppm, the gelling time is significantly reduced. If over 1500 ppm is added the solution aggregates. If less than 800 ppm there is no appreciable reduction in gelling time. It is preferred to add about 1000 ppm of sodium acid ortho or pyrophosphate.

The pH of the mixture of polyol solution and gellant for a satisfactory production of a gel is from about 5 to about 10, preferably 6.5 to 8.5.

The gels obtained according to this invention contain at least 10 weight percent of the polyols, and preferably 30 to about 70 weight percent, at least 0.05 weight percent of calcium sodium pyrophosphate and preferably 0.5 to about 5 weight percent, with the balance being water. Generally, the gel has a gel strength from about 500 dyne/cm$^2$ to about 100,000 dyne/cm$^2$ with 1000 dyne/cm$^2$ to about 40,000 dyne/cm$^2$ being preferred. Gel strength is determined by using a Haake Viscometer (Rotvisco) at the slowest speed, i.e., 0.03 rpm. Additionally, the gels are stable at a temperature up to about 100° C.

The gels obtained in accordance with this invention have a wide variety of uses, for example, a sorbitol gel can be cast into a stick and used as a deodorant in same manner as those which are commercially available.

Numerous gels differing in texture, rheological properties, can be formed by incorporating other cosmetic, pharmaceutical ingredients and other hydrocolloids such as starch, agar, algin, carrageenan, gum arbic, guar gum, pectin, gum tragaranth, sodium carboxymethylcellulose and starch derivatives.

This invention is specifically illustrated by the following examples in which all parts, percentages or proportions are by weight unless otherwise indicated.

EXAMPLE I

A 25 weight percent aqueous solution of calcium chloride is added to a 15 weight percent aqueous solution of tetrasodium pyrophosphate in a suitable vessel until the pH reaches 7. The acicular crystals of calcium sodium pyrophosphate tetrahydrate are formed. The crystals are filtered, washed thoroughly, and dried at 60° C. The calcium sodium pyrophosphate tetrahydrate is then heated at a temperature within the range of 175° to 200° C for a period of 60 minutes until 3.2 moles of water of hydration is removed. The dehydrated solids were then ground. The structure of the material is now amorphous as determined by X-ray diffraction.

The above procedure was followed and a calcium sodium pyrophosphate having 0.8 moles of water of hydration, was obtained.

EXAMPLE II

To a 100 cc of an aqueous sorbitol solution containing 45 weight percent of sorbitol is added 2 grams of the calcium sodium pyrophosphate having 0.8 moles of water of hydration produced in Example I. The solution is agitated and the solution is left quiescent to form a gel at room temperature. In 10 minutes, the mixture started to gel.

The above procedure was followed obtaining a sorbitol gel. The gel had a gel strength of 18,000 dyne/cm$^2$ after 24 hours as determined using a Haake Viscometer (Rotvisco).

EXAMPLE III

The procedure set forth in Example I was repeated with the exception that 2.5 moles of hydration water was removed.

To a 100 cc of an aqueous solution containing 45 weight percent sorbitol was added to 2 grams of the calcium sodium pyrophosphate having 2.5 moles of water. The solution was agitated and then set to a gel. The gel strength by a Haake Viscometer (Rotvisco) was 9,000 dyne/cm$^2$ after 24 hours.

EXAMPLE IV

To a 100 cc of an aqueous solution containing 45 weight percent sorbitol, 2 grams of ground calcium sodium pyrophosphate tetrahydrate is mixed. The same procedure is repeated with calcium sodium pyrophosphate having less than 0.1 mole of water of hydration. In both cases no gelling is observed.

EXAMPLE V

The procedure of Example II is repeated except that sodium acid pyrophosphate ($Na_2H_2P_2O_7$) is added to the solution of polyol in an amount of 0.1 weight percent. The gelling rate is increased.

The above procedure was followed. In another run, monosodium orthophosphate ($NaH_2PO_4$) is substituted for sodium acid pyrophosphate. For comparison purposes, a run was made without the addition of either sodium acid pyrophosphate or disodium orthophosphate. The results are given in the following table.

Table

| Phosphate Used | None | $Na_2H_2P_2O_7$ | $NaH_2PO_4$ |
|---|---|---|---|
| pH | 8.0 | 7.0 | 7.6 |
| Relative Strength for given time in dyne/cm$^2$ | | | |
| 30 min. | 1.0 | 3.2 | 1.1 |
| 60 min. | 1.5 | 4.5 | 2.2 |
| 24 hours | 18,400 | >35,000 | >35,000 |

As can be seen, the gelling rate is increased.

EXAMPLE VI

Two grams of the material prepared in Example I is added to 100 cc of an aqueous solution of glycerine containing 45 weight percent of glycerine at a temperature of 25° C. the glycerine mixture set up to a soft gel.

EXAMPLE VII

The procedure set forth in Example VI is repeated with the exception that mannitol is substituted for glycerine.

EXAMPLE VIII

To a 100 cc of an aqueous sorbitol solution containing 45 weight percent of sorbitol are added 2 grams of the calcium sodium pyrophosphate prepared in Example I and 10 grams of titanium oxide. The mixture gels in about 5 hours to form a soft gel of cream consistency.

EXAMPLE IX

To a 200 cc of an aqueous sorbitol containing 45 weight percent of sorbitol by weight are added 4 grams of the calcium sodium pyrophosphate prepared in Example I, 0.3 g methyl parahydroxybenzoate (i.e., methyl PARASEPT by Heyden) and 0.5 g perfume. The mixture was stirred vigorously for two minutes. The preparation was poured into a rubber stoppered glass tubing having approximately ⅝ inch inside diameter. It was allowed to gel in a rack that kept the tubing in a vertical position. After two to three hours, the cast stick was forced from the tubing by means of a plunger. The casting was cut to proper size to prepare deodorant sticks.

What is claimed is:

1. A process for gelling an aqueous suspension of a polyol, selected from the group consisting of sorbitol, mannitol and glycerine, which comprises adding thereto a calcium sodium pyrophosphate having the formula $CaNa_2P_2O_7 \cdot xH_2O$, where x has a value of from about 0.1 to about 2 in a sufficient amount to bring about gellation whereby a gel is formed having gel strength of about 500 dyne/cm$^2$ to about 100,00 dyne/cm$^2$.

2. A process according to claim 1, wherein said calcium sodium pyrophosphate is present in an amount of from about .1 weight percent to about 10 weight percent, based on the aqueous solution of polyol.

3. A process according to claim 1, wherein said polyol is sorbitol.

4. A process according to claim 1, wherein additionally is added about 1,000 ppm to about 1,500 ppm of sodium phosphates selected from the group consisting of monosodium orthophosphate, disodium orthophosphate, sodium acid pyrophosphate and tetrasodium pyrophosphate.

5. A gel which comprises (1) a polyol, selected from the group consisting of sorbitol, mannitol and glycerine, said polyol being present in an amount of at least about 15 weight percent, based on the total weight of the gel, (2) amorphous calcium disodium pyrophosphate having the formula $CaNa_2P_2O_7 \cdot xH_2O$, wherein x has a value of from about 0.1 to about 2.0, said pyrophosphate being present in an amount of at least 0.05 weight percent, based on the total weight of the gel, and (3) water, said water constituting the balance; said gel having a gel strength of about 100 dyne/cm$^2$ to about 100,000 dyne/cm$^2$.

6. A gel according to claim 5, wherein said polyol is sorbitol.

* * * * *